US009061259B2

(12) United States Patent
Murray et al.

(10) Patent No.: US 9,061,259 B2
(45) Date of Patent: Jun. 23, 2015

(54) CLOUD MIXER AND METHOD OF MINIMIZING AGGLOMERATION OF PARTICULATES

(71) Applicants: Scott Murray, East Lansing, MI (US); Michael Knox, East Lansing, MI (US)

(72) Inventors: Scott Murray, East Lansing, MI (US); Michael Knox, East Lansing, MI (US)

( * ) Notice: Subject to any disclaimer, the term of this patent is extended or adjusted under 35 U.S.C. 154(b) by 0 days.

(21) Appl. No.: 14/215,356

(22) Filed: Mar. 17, 2014

(65) Prior Publication Data

US 2014/0228454 A1 Aug. 14, 2014

Related U.S. Application Data

(62) Division of application No. 13/610,934, filed on Sep. 12, 2012, now Pat. No. 8,715,720.

(60) Provisional application No. 61/573,897, filed on Sep. 14, 2011.

(51) Int. Cl.

| | |
|---|---|
| ***A61K 9/00*** | (2006.01) |
| ***B01F 15/02*** | (2006.01) |
| ***B01F 3/12*** | (2006.01) |
| ***B01F 5/10*** | (2006.01) |
| ***B01F 5/20*** | (2006.01) |

(52) U.S. Cl.
CPC ............... *B01F 15/0254* (2013.01); *B01F 3/12* (2013.01); *B01F 5/106* (2013.01); *B01F 5/205* (2013.01)

(58) Field of Classification Search
None
See application file for complete search history.

(56) References Cited

U.S. PATENT DOCUMENTS

| | | | |
|---|---|---|---|
| 5,230,735 | A | 7/1993 | Murata et al. |
| 2004/0028808 | A1 | 2/2004 | Williams et al. |
| 2008/0309708 | A1 | 12/2008 | Teshima et al. |
| 2010/0102700 | A1 | 4/2010 | Jaiswal et al. |
| 2010/0226722 | A1 | 9/2010 | Walker |
| 2011/0200678 | A1 | 8/2011 | Hwang et al. |

OTHER PUBLICATIONS

U.S. Appl. No. 13/610,934, filed Sep. 12, 2012, Murray.

*Primary Examiner* — Robert A Wax
*Assistant Examiner* — Olga V Tcherkasskaya

(57) ABSTRACT

An apparatus and a methods for dispersing particulate materials prone to agglomeration, in a liquid. Particulate materials are exposed to a liquid and put into that liquid to form a suspension or a dispersion in a controlled method thereby minimizing agglomerates. The method uses mechanical/hydro mixing that prevents the physical deterioration of the particulate material and inhibits agglomeration of the particles. In many cases, these materials may be nanomaterials. Almost all particulate materials can be handled in this manner. This method has been found to be especially useful for preparing solutions of exfoliated graphene and certain drugs.

6 Claims, 3 Drawing Sheets

CLOUD MIXER AND METHOD OF MINIMIZING AGGLOMERATION OF PARTICULATES

This application claims the benefit of earlier filed U.S. provisional patent application Ser. No. 61/573,892, filed Sep. 14, 2011, from which priority is claimed.

BACKGROUND OF THE INVENTION

Particles are more useful if they are capable of being mixed under various conditions without physical damage. Particles are prone to agglomeration and this is especially true when these materials are introduced into liquids. Mixing would not be a problem normally, but certain particles are susceptible to harsh handling.

In the laboratory setting, it is possible to introduce materials into liquids at a very slow rate using methods that are conducive to producing desired properties. This is not always possible when processes are operated on a large scale and require large amounts of materials to be introduced rapidly into liquids prior to mixing and dispersing operations.

The most common methods of introduction involve turbulence and high shear. There are machines that use various methods of introduction by pulling materials into a stream using a vacuum or pressure drop created by the flow of the liquid and the equipment. Typically, equipment of this type does not control the speed of material introduction, or if it does, it does so by using adjustments to the amount of vacuum created in the system.

Both of these techniques expose the material being put into dispersion, to the liquid, in a relatively uncontrolled amount, and then rely on a zone of high pressure and shear immediately upon introduction, to "wet" the material.

The ability of these types of equipment to disperse the particles, and specifically graphite materials, is not satisfactory for many applications.

Thus, it is desirable to have an apparatus and method which can mix the particulate materials rapidly into liquids to give uniform dispersions, and at the same time, not create problems because of harsh handling. Such a method would create a non-agglomeration of the nanomaterials in liquid.

"Dispersions" and "suspensions" are considered to be interchangeable in this disclosure.

THE INVENTION

Figure 2:
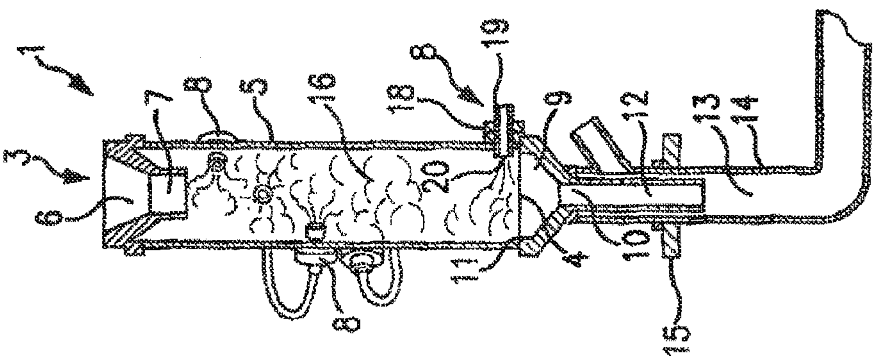
FIG. 2 is a cross sectional view of the cloud mixer of FIG. 1 through line A-A.

Thus, what is disclosed is a method of dispersing particulate material that is susceptible to agglomeration in a liquid. The method comprises providing a particulate material and a misting apparatus. The misting apparatus has a chamber that has a side wall and a plurality of misting nozzles inserted through the side wall.

There is also provided a storage tank for a liquid and a high pressure pump for pumping the liquid from the storage tank to a manifold. There is a plurality of transfer lines for the liquid from the manifold to the misting nozzles and the liquid has a controlled flow through the misting nozzles and into the chamber to form a mist in the chamber.

Then, nanomaterial is fed into the top of the chamber at a controlled rate and allowed to fall through the mist to form a dispersion. The newly formed dispersion is directed to a mixing chamber and transferred to a holding tank.

The dispersion is circulated from the holding tank through an inlet port into the mixing chamber using a high volume pump, wherein the circulating dispersion contacts and mixes with the newly manufactured dispersion through laminar flow.

In another embodiment, there is an apparatus for dispersing a particulate material in a liquid, the apparatus comprising a hollow tubular chamber having an open top, open bottom, and a side wall. The open top has surmounted therein, a feed tube entry component having a feed tube throat smaller in diameter than the open top of the hollow tubular chamber. There is a series of misting nozzles located through the side wall of the hollow tubular chamber.

There is a storage tank for a liquid, a high pressure pump, a manifold, and a plurality of transfer lines. There is a drain funnel having an open bottom end and it is attached at the open bottom of the hollow tubular chamber. The mixing chamber has an inlet port through a side wall.

There is a chamber drain attached to the open bottom end of the drain funnel, the chamber drain being surrounded by a cylindrical covering having an outside wall. There is a support plate surrounding the cylindrical covering and attached to it.

Also included is a holding tank and a high volume pump, wherein the holding tank is connected to the inlet port via the high volume pump.

In addition, there is yet another embodiment which is product obtained by the process as set forth just Supra.

A further embodiment is a method of dispersing a particulate material that is susceptible to agglomeration in a liquid, the method comprising providing a particulate material and a misting apparatus, wherein the misting apparatus has a chamber having a side wall and a plurality of misting nozzles inserted through the side wall.

There is also provided a storage tank for a liquid, a high pressure pump for pumping the liquid from the storage tank to a manifold and a plurality of transfer lines for the liquid from the manifold to the misting nozzles, the liquid having a controlled flow through the misting nozzles and into the chamber to form a mist in the chamber.

A nanomaterial is fed into the top of the chamber at a controlled rate and allowed to fall through the mist to form a dispersion. The newly formed dispersion is collected in a mixing chamber and transferred to an eductor.

The dispersion from the eductor is circulated through to a holding tank and back to the eductor using a high volume pump, wherein the circulating dispersion contacts and mixes with the newly manufactured dispersion through laminar flow.

In addition, there is an apparatus for dispersing a particulate material in a liquid, wherein the apparatus comprises a hollow tubular chamber having an open top, open bottom, and a side wall.

The open top has surmounted therein, a feed tube entry component having a feed tube throat smaller in diameter than the open top of the hollow tabular chamber. There is a series of misting nozzles located through the side wall of the hollow tubular chamber.

There is a storage tank for a liquid, a high pressure pump, a manifold, and a plurality of transfer lines. There is a drain funnel having an open bottom end and it is attached at the open bottom of the hollow tubular chamber. A chamber drain is attached to the open bottom end of the drain funnel, the chamber drain being surrounded by a cylindrical covering having an outside wall.

There is a support plate surrounding the cylindrical covering and attached to it. There is an eductor having an inlet pipe, an inlet port, and an outlet port, a holding tank, and a high volume pump, the holding tank being connected to the eductor through the inlet port via the high volume pump.

A final embodiment is a product obtained by the process set forth just Supra.

DETAILED DESCRIPTION OF THE INVENTION

Figure 1:
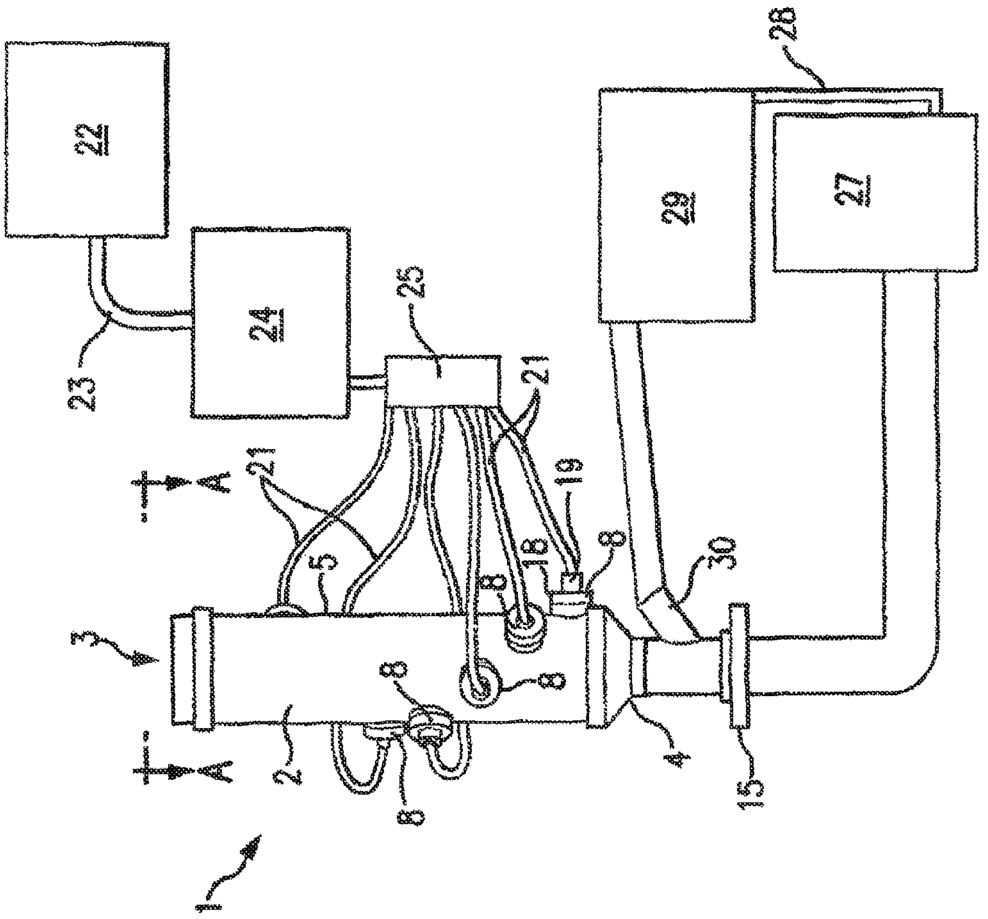
FIG. 1 show a full front view of a cloud mixer of this invention without the eductor.

Turning now to a detailed description of the invention, there is shown in FIGS. 1 and 2, a cloud chamber 1 of this invention. The cloud chamber 1 is comprised of a hollow tubular chamber 2 having an open top 3 and an open bottom 4. There is a side wall 5. The open top 3 has surmounted in it, a feed tube entry component 6 (FIG. 2) having a feed tube throat 7 smaller in diameter than the open top 3 of the hollow tubular chamber 2. This feed tube entry is for the feeding of particles into the cloud chamber 1.

There is a series of misting nozzles 8 located and projecting through the side wall 5 such that liquid can be forced through the misting nozzles 8 into the interior of the cloud chamber 1. The misting nozzles 8 are comprised of a nozzle mount 18, a nozzle port 19 for input of liquid, and a nozzle orifice 20, sufficient to deploy a mist into the chamber 1.

There is a drain funnel 9 having an open bottom end 10 and this drain funnel 9 is attached to the bottom end 11 of the open bottom 4. There is a chamber drain 12 attached to the open bottom end 11 of the drain funnel 9 wherein the chamber drain 12 is surround by a cylindrical covering 13 having an outside wall 14. The cylindrical covering 13 has a support plate 15 surrounding the cylindrical covering 13 and such covering 15 is attached to the cylindrical covering 13.

The cloud chamber 1 is relatively large in comparison to the transfer lines 21 into which the liquid that is added is flowing. An increase in size allows for control of the pressure drop created by the low pressure area in the cloud chamber 1.

The liquid supplied to the misting nozzles 8 is held in a holding tank 22 and fed through line 23 into a high pressure pump 24. From there, the liquid is pumped into the manifold 25 which disperses the liquid to the transfer lines 21 and into the nozzles 8.

As materials are fed at a controlled rate into the top of the cloud chamber 1, they fall through a mist cloud 16 and to a high degree come into contact with the mist droplets 16 of the liquid. At the bottom end 11 of the cloud chamber 1, both the vacuum created, and the cumulative flow of the liquid 22, now containing material particles is introduced into the stream.

As the newly formed dispersion drops into the bottom of the chamber 1, it enters a storage tank 27 and is transferred by way of line 28 as the high volume pump 29 transfers the mixed dispersion of the storage tank 27 back to the inlet port 30 at the bottom of the chamber 1. In this manner, there is a continued mixing of the stored dispersion with the newly formed dispersion and this creates a uniform product.

While some turbulence occurs at the point of introduction into the stream, the pressure and shear at this point are not severe. The combined liquid and material particles can then be introduced to further processing operations.

Figure 3:
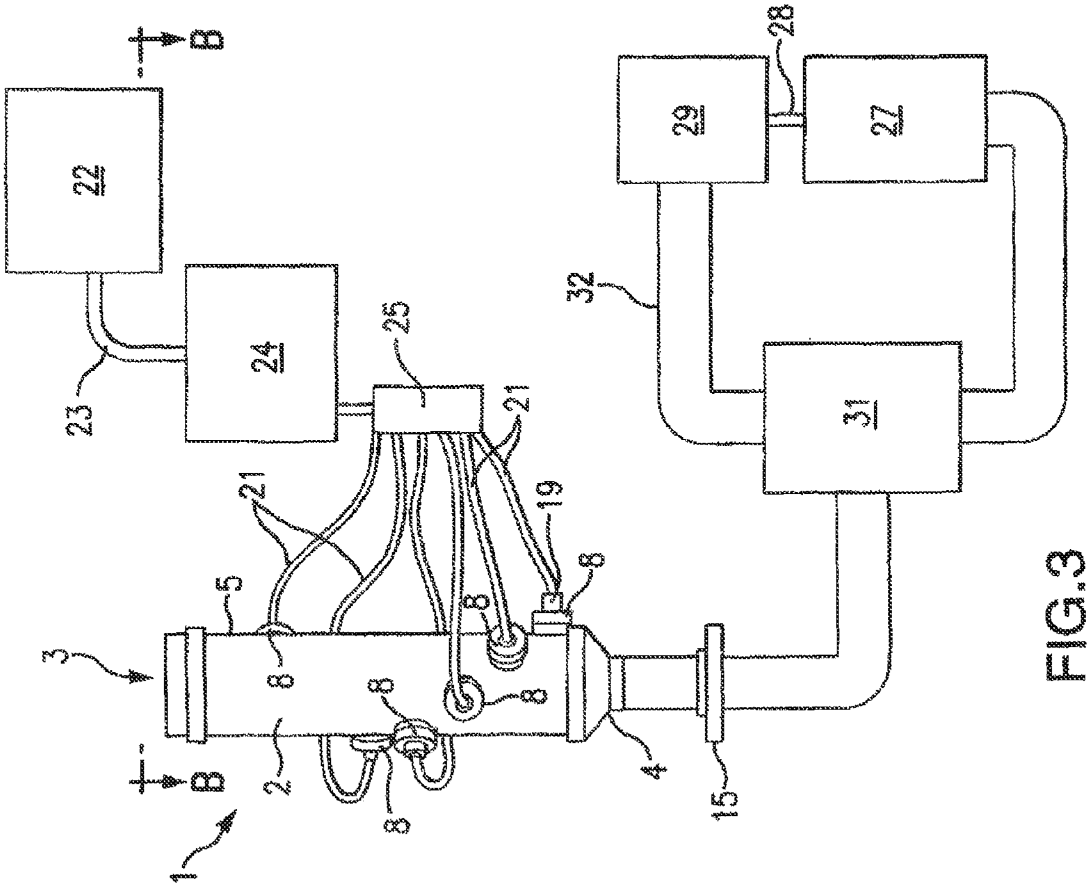
FIG. 3 is a full front view of a cloud mixer of this invention with an eductor.
Figure 4:
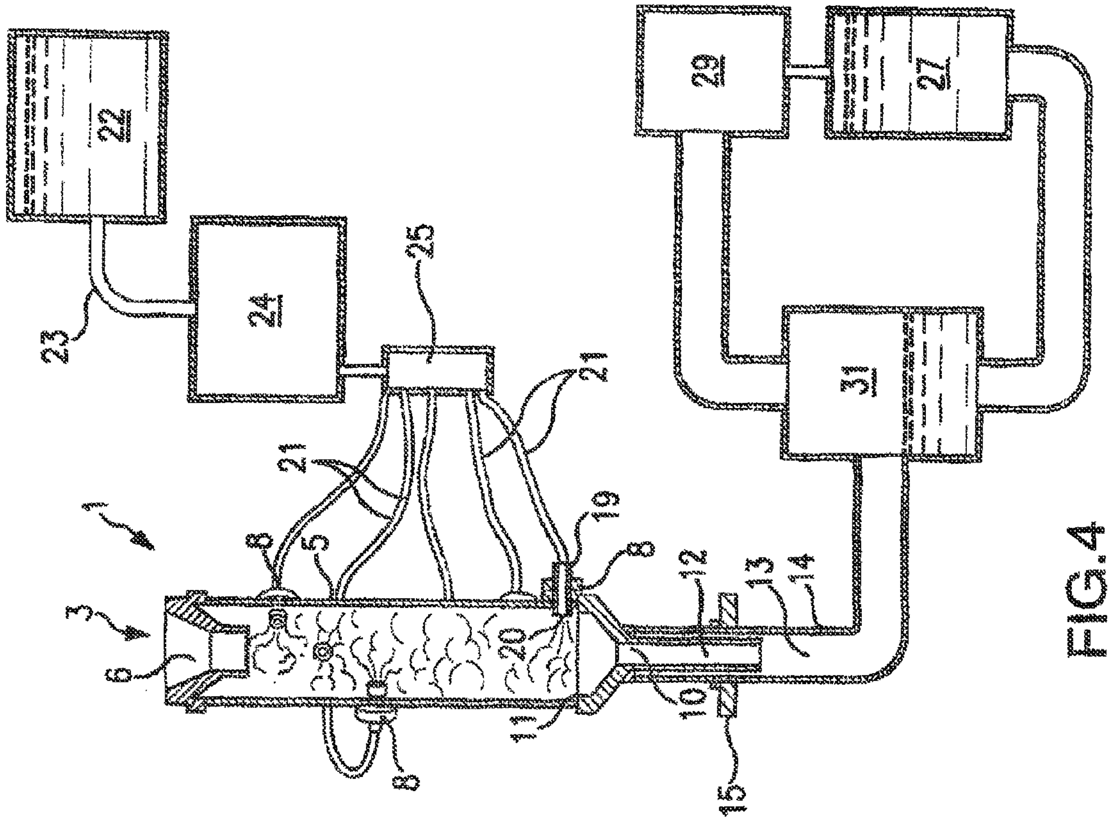
FIG. 4 is a cross sectional view of the cloud mixer of FIG. 3 through line B-B.

In another embodiment and turning now to FIGS. 3 and 4, there is shown a cloud chamber 1 of this invention in which like components have like designated numbers, there is shown the use of an eductor 31 for re-circulating the newly formed dispersion.

In this apparatus, the newly formed dispersion drains to an eductor 31 and is moved from there is a holding tank 27 by high volume pump 29 and then back, into the eductor via line 32. The dispersion is circulated through the eductor 31, and storage tank 27 in a continuous manner until the dispersion is uniform in character.

Any liquid can be used in the apparatus of this invention that is compatible with the particulate material, and can be expelled through a misting nozzle, and preferred are alcohols, especially isopropyl alcohol and n-propanol and water, or a mixture of alcohol and water. In using the alcohols of this invention, it is not necessary to use surfactants, however, one can use surfactants if desired. When water is used, it is preferred to use surfactants.

Using the apparatus as described Supra, there is a method of dispersing a particulate material in a liquid, the method comprising providing a particulate material and a misting apparatus as described, Supra.

After the apparatus is set up, that is, with provisions for supplying a liquid, to the apparatus through the nozzles, a particulate material such as nanoplatelets, nanotubes, or any other material prone to agglomeration, is fed into the top of the chamber at a controlled rate which is determined by the condition of the exiting dispersion from the chamber.

The nozzles are comprised of materials compatible with the solutions being mixed. These nozzles have small orifices, typically less than 0.050 inches, for low viscosity solutions, those approximately 1 centipoise or less. The nozzle orifices size may be increased as the viscosity of the solution increases. Some nozzles may include filters to insure the nozzles do not become plugged, although these filters are not important to the performance of the device.

The ratio of the liquid component to the solid components can vary until the educator fails to create a pressure drop. These ratios will vary with the amount of solution being processed and will require changes to the size of the eductor. The rate of feed may vary from a few grams/minute (600 grams/hour) to higher rates. The size of the cloud mix chamber and the ability to create a pressure drop (vacuum) dictates the maximum rate.

The inventor herein has utilized a cloud chamber 1 that has the approximate dimensions of 4 to 4½ inches in diameter to about 30 to 36 inches in length and has successfully shown a mix at up to 10 Kg/hour. It is believed by the inventor herein that this can easily be increased up to 50 Kg/hour as the cloud mixer is enlarged.

The particulate material is allowed to free fall through the misting liquid which eventually forms a dispersion before the mixture of the particulate material and liquid fall to the bottom of the chamber.

The particulate material dispersion is collected at the bottom of the apparatus and is ready for additional uses or treatment.

Thus, the particulate materials are exposed to a liquid and put into that liquid in a controlled method thereby minimizing agglomerates. The method uses mechanical/hydro mixing that prevents the physical deterioration of the particles.

Almost all particulate materials can be handled in this manner. The method is very useful for particles having an average particle size of about 200 microns or less, wherein at least one dimension of the particle has an average of less than 25 nanometers. Although it is preferred for the particulate materials of this invention to be thin, that is, on the order of 6 to 16 nanometers, the size of the particle may be several hundred microns in width. This method has been found to be especially useful for preparing dispersions of exfoliated graphene and dispersions of certain drugs.

What is claimed is:

1. A product obtained a method comprising:

i. providing a particulate material;

ii. providing a misting apparatus, said misting apparatus having a chamber having a side wall and a plurality of misting nozzles inserted through said side wall;

iii. providing a storage tank for a liquid;

iv. providing a high pressure pump for pumping said liquid from said storage tank to a manifold;

v. providing a plurality of transfer lines for said liquid from said manifold to said misting nozzles, aid liquid having a controlled flow through said misting nozzles and into said chamber to form a mist in said chamber;

vi. feeding the particulate material into the top of said chamber at a controlled rate and allowing said particulate material to fall through said mist to form a dispersion;

vii. collecting said newly formed dispersion in a mixing chamber and transferring said newly formed dispersion to a holding tank;

viii. circulating said dispersion from said holding tank through an inlet port into said mixing chamber using a high volume pump, wherein said circulating dispersion contacts and mixes with said newly manufactured dispersion through laminar flow.

2. A product as claimed in claim 1 wherein the product is a graphite material such as graphene.

3. A product as claimed in claim 1, wherein the product is a drug.

4. A product obtained by a method of dispersing a particulate material that is susceptible to agglomeration in a liquid the method comprising:

a. providing a particulate material;

b. providing a misting apparatus, said misting apparatus having a chamber having a side wall and a plurality of misting nozzles inserted through the side wall;

c. providing a storage tank for a liquid;

d. providing a high pressure pump for pumping said liquid from the storage tank to a manifold;

e. providing a plurality of transfer lines for said liquid from the manifold to said misting nozzles, said liquid having a controlled flow through said misting nozzles and into said chamber to form a mist in said chamber;

f. feeding said particulate material into said top of said chamber at a controlled rate and allowing said particulate material to fall through said mist to form a dispersion;

g. collecting newly forted dispersion in a mixing chamber and transferring said newly formed dispersion to an eductor;

h. circulating said dispersion from said eductor through to a holding tank and back to said educator using a high volume pump, wherein said circulating dispersion contacts and mixes with said newly manufactured dispersion through laminar flow.

5. A product as claimed in claim 4 wherein the product is a graphite material such as graphene.

6. A product as claimed in claim 4 wherein the product contains a drug.

* * * * *